(12) United States Patent
Weindel et al.

(10) Patent No.: US 6,214,549 B1
(45) Date of Patent: Apr. 10, 2001

(54) METHOD OF DETECTING A SUBSTANCE TO BE ANALYZED

(75) Inventors: Kurt Weindel, Wielenbach; Christoph Seidel, Weilheim; Gerhard Lassonczyk, Peissenberg, all of (DE)

(73) Assignee: Roche Diagnostics GmbH, Mannheim (DE)

(*) Notice: Subject to any disclaimer, the term of this patent is extended or adjusted under 35 U.S.C. 154(b) by 0 days.

(21) Appl. No.: 09/051,079

(22) PCT Filed: Oct. 8, 1996

(86) PCT No.: PCT/EP96/04358

§ 371 Date: Sep. 10, 1998

§ 102(e) Date: Sep. 10, 1998

(87) PCT Pub. No.: WO97/13874

PCT Pub. Date: Apr. 17, 1997

(30) Foreign Application Priority Data

Oct. 12, 1995 (DE) .............................. 195 37 952

(51) Int. Cl.[7] .............................. C12Q 1/68; C02H 21/02; C02H 21/04; C12N 15/00
(52) U.S. Cl. .............................. 435/6; 536/23.1; 536/24.3; 935/76; 935/22; 935/28
(58) Field of Search .............................. 435/6; 536/23.1, 536/24.3; 935/76, 77, 78

(56) References Cited

U.S. PATENT DOCUMENTS

| | | | |
|---|---|---|---|
| 5,344,757 | * | 9/1994 | Holtke et al. .............................. 435/6 |
| 5,424,188 | * | 6/1995 | Schneider et al. .............................. 435/6 |
| 5,424,413 | * | 6/1995 | Hogan et al. .............................. 536/24.31 |
| 5,437,977 | * | 8/1995 | Segev .............................. 435/6 |
| 5,486,455 | * | 1/1996 | Stults .............................. 435/6 |
| 5,571,677 | * | 11/1996 | Gryaznov .............................. 435/6 |
| 5,624,802 | * | 4/1997 | Urdea et al. .............................. 435/6 |
| 5,635,352 | * | 6/1997 | Urdea et al. .............................. 435/6 |
| 5,695,936 | * | 12/1997 | Mandrand et al. .............................. 435/6 |
| 5,719,262 | * | 2/1998 | Buchardt et al. .............................. 530/300 |

FOREIGN PATENT DOCUMENTS

| | | |
|---|---|---|
| 0 137 515 | 4/1985 | (EP) . |
| WO 90/13667 | 11/1990 | (WO) . |
| WO9108307 | * 6/1991 | (WO) . |
| WO 95/01365 | 1/1995 | (WO) . |
| WO9522623 | * 8/1995 | (WO) . |

OTHER PUBLICATIONS

Matthews et al., Review: Analytical Strategies for Use of DNA Probes. Analytical Biochemistry 169:1–25 (1988).*
Boehringer Mannheim Product Information: "PCR Eliza" (1994).*
The Stragene Catalog, p. 39 (1988).*

* cited by examiner

*Primary Examiner*—Ethan Whisenant
(74) *Attorney, Agent, or Firm*—Arent Fox Kintner Plotkin & Kahn, PLLC

(57) ABSTRACT

The invention concerns a method of detecting a substance to be analyzed in a sample by contacting the sample with a probe which contains nucleobases and two or more non-nucleosidic marker-promoting groups in conditions in which the substance to be analyzed binds indirectly or directly to the probe. The method enables the binding product to be detected. The probe is preferably branched.

22 Claims, 7 Drawing Sheets

5'- XTT TTT TTT TTA TAG GGG CAT TTG GTG GTC T -3'
(SEQ ID NO 2)

5'- AGA CCA CCA AAT GCC CCT AT -3' (SEQ ID NO 3)

5'- XTTTTTTTTXTTTTTTTTTTATAGGGGCATTTGGTGGTCT -3'
(SEQ ID NO 4)

5'- XTTTTTTTTTTTTTTTTTTXTTTTTTTTTT-
ATACGGGCATTTGGTGGTCT -3' (SEQ ID NO 5)

5'-
XTTTTTTTTTXTTTTTTTTTTTTXTTTTYTTTTXTTTTYTTTTTATAGGGGCA
TTTGGTGGTCT -3' (SEQ ID NO 6)

X: DNP LABELED
Y: H, AM III- MALEINIMIDO OR AM III- MALEINIMIDO-S-
 -TTTTTTTTTXTTTTTTTTTXT -3'

5'- XTTTTTTTTTXTTTTTTTTTXTTTTYTTTTXTTT-
-TYTTTTTATAGGGGCATTTGGTGGTCT -3' (SEQ ID NO 7)

METHOD OF DETECTING A SUBSTANCE TO BE ANALYZED

Subject matter of the invention is a method of detecting a substance to be analyzed in a sample using a probe which contains nucleobases.

The detection of low-concentration substances to be analyzed in samples has become very important in clinical testing. As a result of numerous developments, the detection limit for substances to be analyzed has been lowered considerably compared with earlier tests. This development has had a particularly strong impact in the field of nucleic acid detection. Many of the detection systems used today, however, involve complex working steps or use reagents that are very complex to manufacture. These systems have many disadvantages.

In U.S. Pat. No. 4,683,202, a method for detecting nucleic acids is described that is based on the amplification of segments of an original nucleic acid. This method has become known as the polymerase chain reaction. A disadvantage of this method, however, is that the results are difficult to quantify.

Results are easier to quantify when nucleic acid probes are used with which stoichiometric hybridization takes place. Unfortunately these methods are insensitive.

In a further development of the traditional hybridization test, it was therefore proposed that a number of identical nucleotide sequences be bound with each probe. The hybrid consisting of analyte nucleic acid and probe was detected by hybridizing a number of secondary probes that were complementary to these identical nucleotide sequences. A number of documents that describe the prior art discuss the most favorable arrangement of the many identical nucleotide sequences in the probe or in a set consisting of probes that are capable of hybridizing—and, therefore, aggregating—with each other (e.g., U.S. Pat. No. 5,424,188; EP-B-0 248 896 B1; U.S. Pat. No. 5,424,413; U.S. Pat. No. 5,437,977). It is stated in U.S. Pat. No. 5,424,188, for instance, that the identical nucleotide sequences can be attached to each other in linear fashion. The chain of identical nucleotide sequences produced can also be formed into a closed ring. It is stated in U.S. Pat. No. 5,124,246 that the identical nucleotide sequences can be bound to each other by means of a branched structure. A distinction is made in this case between fork-like branchings and comb-like branchings. A number of potential technical embodiments have been described for the branchings (Nucleic Acids Research 16/11, 4937–4965, Gene 61, 253–264, Nucleic Acids Research 17/17, 6959–6967, Clinical Chemistry 35/8, 1571–1575 (1989), Bioorganic and Medicinal Chemistry Letters 4/8, 1011–1018 (1994), Nucleic Acids Research Symposium 24, 197–200 (1991), and Clin. Chem. 39/4, 725–726 (1993)). In WO 95/01365, a branching method is also described in which the lateral arms are bound to a special backbone by means of a reaction between phosphorothioates and haloacyl groups. Methods in which the probe has a number of identical nucleotide sequences for hybridizing with secondary probes can often lead to increased calibration curve sensitivity. The probes required for this, however, are 1) difficult to manufacture, and 2) the labelled probes do not stoichiometrically saturate the nucleic acid sequences on the probes. The test sensitivity achieved is therefore much less than that of the PCR method (AIDS 7/suppl., 11–14 (1993); J. Med. Virol. 43, 262–268 (1994); J. Infect. Dis. 170, 1172–1179 (1994); AIDS Res. & Human Retrovir. 11/3, 353–361 (1995)).

The one feature that all of these concepts have in common is that at least two different types of probes—one of which is present in great numbers—are aggregated into one detectable amplification unit based on the principle of hybridization of single-stranded overhangs.

Object of the invention was, therefore, to improve the prior art and, in particular, to develop a sensitive method of detection that can be quantified directly.

Subject matter of the invention is therefore a method for detecting a substance to be analyzed in a sample by contacting the sample with a probe which contains nucleobases and two or more non-nucleosidic, label-attracting groups under conditions in which the substance to be analyzed binds indirectly or directly to the probe and detecting the binding product.

A substance to be analyzed according to the invention can be any ingredient in a sample. Preferably, however, the substance to be analyzed is a molecule that can be detected immunologically or by means of base pairing. Immunologically detectable substances to be analyzed are, for instance, antibodies, antigens or haptens. Nucleotides are substances to be analyzed that can be detected by means of base pairing. They include ribonucleic acids and deoxyribonucleic acids. These types of substances to be analyzed can be detected in practically any sample using the proposed method. In many cases, however, it is preferable to pretreat the sample so that the substance to be analyzed is present in a form that facilitates detection. This includes releasing the substance to be analyzed from compartments, e.g., cells, in which the analyte was originally enclosed. The substance to be analyzed can itself be a compartment, however, if it has detectable components on its surface, such as surface antigens. In addition, the actual substance to be analyzed can be amplified before the method provided by this invention is carried out, e.g., using the PCR, but preferably only to the degree that the amplification can still be quantified. Blood, urine, sputum or swabs have proven to be suitable fluids from which a sample suitable for detection can be produced. Another possible preparation step is to liquify viscous samples or to partially purify the analyte, e.g., by immobilizing it on a solid phase. The analyte can be present in a liquid, e.g., in dissolved or suspended form. The analyte can also be bound to a solid phase, however. Suitable solid phases include latex particles, magnetic particles, or vessel walls.

A probe according to the present invention is a molecule that has a first nucleic acid-type portion, and a second portion that is analyte-specific or that promotes contact with the analyte. The nucleic acid-type portion contains nucleobases on a backbone. Nucleobases include the naturally occurring bases A, G, C, T, and U, or any bases derived therefrom. A potential backbone is the natural sugar phosphate structure. Molecules that have a polyamide backbone were also described recently (e.g., in WO 91/20702). The probe can bind the analyte directly or indirectly by means of the analyte-specific portion. In cases of direct binding, the nature of the analyte-specific portion can depend on the type of substance to be analyzed. If the substance to be analyzed is immunologically active, binding can take place with the partner that is immunologically complementary to the analyte. To detect an antigen, for instance, a probe can therefore be used that contains an antibody to this antigen that is bound covalently or non-covalently to the nucleic acid-type portion. If the substance to be analyzed is a nucleic acid, the probe contains a nucleobase sequence that is complementary to one part of the base sequence of the analyte. An indirect binding of the probe to the analyte can be achieved by directing the analyte-specific portion against a part of a promotor probe that can bind with the analyte. The promoter probe therefore preferably contains an analyte-specific portion and a portion that is capable of binding with the analyte-specific portion. In this case it is preferable for the probe and the promoter probe to bind with each other by means of base pairing. In this case, a promoter probe is preferably selected that has a portion that is complementary to the analyte and a portion that is complementary to the probe. The advantage of this method is that a number of relatively simply constructed promoter probes be used that correspond to the number of analytes to be detected in order to detect various analytes, but only requires one relatively complex probe.

The nucleic acid-type portion of the probe is designed in such a way that it cannot form hybrids with other nucleic acids found in the reaction mixture or sample mixture. The nucleic acid-type portion can be linear. The nucleic acid-type portion is usually sterically complex, however, and a preferred embodiment is branched many times within itself. This portion is preferably branched in chemically covalent fashion and, especially preferred, by means of functional groups between (deoxy-)ribose units. The portion also preferably contains a number of identical nucleotide sequences. The manufacture of branched molecules of this nature is described in detail in the prior art described earlier. A few concepts for manufacturing branched, nucleic acid-like portions are explained below.

According to one embodiment, nucleic acids that are made by inserting $N^4$-(N-(6-trifluoroacetyl-amidocaproyl)-2-aminoethyl)-2'-deoxycytidine during phosphoramidite synthesis are cross-linked using p-phenylene diisothyocyanate (DITC) as a homobifunctional linker, and a suitable, double-stranded fraction is isolated from the product mixture, e.g., star-structured multimers. The manufacture of these multimers is described in "Luminescence Immunoassay and Molecular Applications" (1990, Editor: Knox Van Dyke, CRC Press, Boca Raton, USA). Another possibility for branching is provided by branching monomers that have a total of three hydroxyl groups per nucleotide. The additional hydroxyl group that is orthogonal to the 5', 3'-axis can be bound with cytidine in position N4 by means of a hexamethylene group, for instance. Both the 5'-hydroxyl group and the hydroxyl group located on the base (which formerly had the same protective group) react with a nucleoside phosphoramidite during oligonucleotide synthesis according to phosphoramidite procedure. As a result, the oligonucleotide chain being constructed branches every time a branching monomer is used. By varying the protective groups, a linear DNA strand can be synthesized that has branching points everywhere that these branching monomers were incorporated. Subsequent selective cleavage of the protective group of the second hydroxyl group enables the lateral strands to be synthesized separately. These secondary sequences project from the primary sequence like teeth in a comb (comb structures). These methods are described, for instance, in Nucleic Acids Research 17/17, 6959–6967 (1989) and Nucleic Acids Research Symposium 24, 197–200 (1991).

A core of the invention is the fact that the probe has two or more label-attracting, non-nucleosidic groups within its nucleic acid-like portion. The invention therefore differs from the prior art in that the long, identical nucleotide sequences—which have been used previously as label promoters—are replaced with low molecular, relatively small, non-nucleosidic groups that are incorporated in comparatively close intervals (and are preferably spaced in flexibly away from the backbone). These label-attracting groups are sterically not very complex. Preferable label-attracting groups are relatively small, immunologically detectable groups such as haptens. Especially preferred in terms of the invention are well-soluble haptens that represent a strong antigenic determinant. Candidates include digoxigenin (U.S. Pat. No. 5,344,757), nitrophenols (such as dinitrophenol or nitro-iodophenol), and especially sugars, e.g., lactosamine, or suitable pharmaceuticals. Other examples include the 4-hydroxyl-3-nitro-phenacetyl group (NP), e.g., coupled to an amino spacer such as amino caproic acid as carboxamide via EDC, and further activated by esterification with NHS to form (N-hydroxysuccinimidyl)-ε-aminocaproyl-NP-carboxamide (this enables aminoalkyl-derived phosphonate bridges, nucleic bases or sugars to be attacked, for instance), the 4-hydroxy-3-iodo-5-nitro-phenacetyl group (NIP), e.g. coupled to an amino spacer such as amino capronic acid as a carboxamide via EDC, and further activated by means of esterification with NHS to form (N-hydroxysuccinimidyl)-ε-amino caproyl-NIP-carboxamide (this enables aminoalkyl-derived phosphonate bridges, nucleic bases or sugars to be attacked; specific <NIP>-antibodies are described) and 1-dimethoxy trityl-3-O-(N-(2,4-dinitrophenyl)-3-aminopropyl)-triethylene glycol)-glyceryl-2-O-(cyanoethyl)-(N,N-diisopropyl)-phosphoramidite (DNP-TEG) (DNP-TEG can be inserted directly using the phosphite method during DNA synthesis; specific <DNP>-antibodies are described).

The label-attracting groups can be inserted into the nucleic acid-type portion after it is synthesized. This can be accomplished, for instance, by reacting the nucleic acid-specific portion with compounds that are capable of bonding covalently with groups of nucleic acids. These include reagents in particular that can react with functional groups attached to nucleic acids, e.g., exocyclic amino groups of bases. A suitable method is described in EP-A-0 173 251, for instance. It is also possible to manufacture the label-attracting group by photocoupling the nucleic acids with a reagent that can be photoactivated. A method of this nature is described in U.S. Pat. No. 5,344,757, for instance. This patent describes a label using a digoxigenin group.

It is also possible, however, to use the label-attracting group in the form bound to mononucleotide components that was already used during synthesis of the nucleic acid-type portion. Phosphoramidites can be used in phosphoramidite synthesis, for instance, in which label-attracting groups or protected precursor groups are bound to exocyclic amino groups of a base or to the internucleoside phosphodiesters that are formed.

The probes according to the invention are preferably single-stranded, chemically synthesized compounds.

Another possible method of manufacturing is based on the synthesis method described in WO 95/01365. It is based on the very efficient coupling of thiophosphate or dithiophosphate groups and haloacyl or haloalkyl groups. Thiophosphate and betabromoacetamide functions that couple and form thiophosphorylacetamide bridges are preferably used. Branched multimers that can be used as the nucleic acid-type portion can be made as follows. In the first step, an initial oligonucleotide that is amino or aminoalkyl-derivatized on the 5'-end is reacted with N-hydroxysuccinimedyl-beta-bromo-acetate, forming a terminal beta-bromoacetamido function. In the second step, a second oligonucleotide is functionalized as 3'-O-phosphoryl-(2-aminomethyl-) ethyl-thiophosphate ester on the 3' end. The terminal thiophosphate group of the second oligonucleotide then reacts, with a nucleophilic attack on the bromo-substituted beta-C atom on the 5'-end of the first oligonucleotide, and both oligonucleotides are ligated. The aminomethyl function is then activated into a beta-bromoacetamido function via condensation with N-hydroxy succinimidyl-beta-bromoacetate.

Larger pieces of oligonucleotides can be manufactured by performing corresponding functionalization steps on the 3' and 5'-ends of numerous oligonucleotides and performing the steps described above. These oligonucleotide pieces have many finctionalized beta-bromoacetamido groups, which represent potential branching points. Activatable amino groups can also be inserted directly into the oligo-nucleotide strand using amino alkyl phosphite derivatives during phosphoramidite synthesis. The advantage of this method is that the primary sequence with potential branch-ing points can be thoroughly synthesized on a CPG carrier. In a subsequent step, a third oligonucleotide—which was manufactured by inserting nucleotides that were function-alized using a label-attracting group—is converted to thio-phosphate ester on the 5'-end. Branched multimers can now be made directly (without templates) by reacting this oligo-nucleotide with the inserted beta-bromoacetamido func-tions. These branched multimers represent the basis for the desired signal amplification based on the number of branch-ing points and detectable labels per branching. Unlike the method described in WO 95/01365, relatively short third oligonucleotides can be inserted in the method according to this invention. As described above, they are preferably already labelled with a label-attracting group when attached to the branching points, e.g., when they are synthesized by means of the phosphoramidite method (e.g., per EP-A-0 399 330).

The label-attracting group is preferably detected indi-rectly. It is preferably detected using a conjugate of a group displaying affinity with the label-attracting group, and a signal-producing component. Such groups displaying affin-ity are groups, for instance, that react immunologically with the label-attracting group and bind the conjugate to the label-attracting group. In the case of haptens, antibodies directed against this hapten can therefore be used as groups displaying affinity. When the hapten is digoxigenin, anti-bodies against digoxigenin are available to form conjugates.

Signal-producing components according to the invention are groups that can either be detected directly or—preferably—transformed into a detectable component in a chemical reaction. Especially preferred signal-producing components are relatively small proteins, espe-cially the calcium-activatable photoproteins. A family of molecular systems capable of producing luminescence falls under the concept $Ca^{2-}$-activatable photoproteins. They share the following characteristics:

a. Physico-chemical Aspects
  a reaction complex in final form consisting of a proteina-ceous catalyst (=apo-photoprotein), an organic-chemical substrate—which is firmly yet non-covalently bound, and which represents the actual emitter (=luminescent substance)—and molecular oxygen, which is also firmly fixed (probably covalently protein-bound as hydroperoxide). The molecular oxygen is required to initiate the luminescence reaction (=oxidant)
  differs from enzyme systems in that all components required for the luminescent reaction are bound
  has a relative molecular mass of about 22,000 daltons
  "coelenterazine" ([2-(p-hydroxybenzyl)-6-(p-hydroxyphenyl)-8-benzyl-7-hydroiimidazopyrazine-3-on] is the luminescent substance
  emission peak wavelength ($\mu$ max) is in the blue range (approx. 470 nm)
  the luminescent reaction is initiated by the binding of 2–3 $Ca^{2+}$ ions to the apo-photoprotein
  $Ca^{2+}$ binding domains are present in the apo-photoprotein in the form of EF hand (=helix-loop-helix) structures
  luminescent reaction does not depend on ambient oxygen, i.e., the complete photoprotein luminesces in the pres-ence or absence of $O_2$ in the surrounding atmosphere
  photoprotein reaction takes place in the form of flash kinetics, i.e., a concentrated light emission results from the addition of $Ca^{2+}$ ions (cf. Blinks J. R., et al., Pharmacological Reviews 28/1, 1–93, 1976)
b. Molecular Biological Aspects
  functional apo-photoproteins with a peptide length of 189–196 amino acids
  high concordance between nucleobases and amino acide sequences (>60% homology) of the individual repre-sentatives from the family of $Ca^{2+}$-activatable photoproteins, as illustrated clearly by the cloning of aequorin (Prasher D., et al., Biochemical and Biophysi-cal Research Communications 126/3, 1259–1268, 1985; Prasher, D., et al., Methods in Enzymology 133, 288–299, 1986; Prasher D., et al., Biochemistry 26, 1326–1332, 1987; Cornier M., et al., Photochemistry and Photobiology 49/4, 509–512, 1989), Obelin (Illarionov Boris A., et al., Gene 153, 273–274, 1995), Clytin (Inouye S. & Tsuji F., FEBS 315/3, 343–346, 1993) and Mitrocomin (Fagan T. F., et al., FEBS, 333/3 301–305, 1993).

Of all members of this family of $Ca^{2+}$-activatable photoproteins, aequorin has been used most frequently in recent years with receptor-ligand binding assays. Preferred proteins include, e.g., obelin, halistaurin (=mitrocomin), phiallidin (=clytin) or aequorin. These proteins all emit a light signal when they are activated, which makes it possible to determine their quantity or presence by measuring the light intensity. The use of such photoproteins in traditional tests, and the mechanism by which it leads to signal formation, is described, for instance, in Cornier, M. L. et al., Photochem. & Photobiol. 49/4, 509–512 (1989) or Smith, D. F. et al. in "Bioluminescence and Chemiluminescence: Cur-rent Status (P. Stanley & L. Krick, eds.), John Wiley and Sons, Chichester, U.K. 1991, 529–532. The advantages of these signal-producing components are a shorter measuring time, increased quantum yield compared with other lumi-nescence labelling systems, and a reduced reagent-induced background, i.e., the technical detection range of the lumi-nometer that can fully exploited, and a broader dynamic range of measurement. The relatively small spatial require-ment of the calcium-activatable photoproteins and their cofactors greatly reduces the size of the probe complex created after the conjugate binds. In addition, these calcium-activatable photoproteins do not interact with DNA structures, as is the case with acridinium salts or various chromophores, for instance.

Surprisingly—and contrary to the general opinion—the absence of enzymatically catalyzed signal multiplication with this method as compared with enzyme labelling is more than outweighed in the proposed invention by the combi-nation of minimal non-specific binding of small aequorin conjugates, minimal chemical noise from the label and the trigger, high specific photoprotein activity, and a very pre-cise measurement of aequorin light flashes at a high signal/noise ratio.

The signal-producing components and the components displaying affinity to the label-attracting group are prefer-ably attached by means of a well-solvatable linker with a length of at least 4 and preferably at least 8 atoms. This means that the degree of conformational freedom is increased and there is less steric hindrance. In turn, this can mean that the basic binding reactions can take place more quickly. A core of the invention is the fact that the distance between adjacent signal-producing components bound to the probe can be very small with the present invention. This is achieved in particular when the nucleotide repeat units used in the prior art are replaced with a nucleoside derivative labelled with a label-attracting group. The distance between the midpoints of two adjacent label-attracting groups on one nucleotide strand is preferably smaller than 18 or 15 nucleotides, yet larger than 3 nucleotides, with the present invention.

The distance between branching points in chemically covalently branched multimeric molecules is preferably less than 7 nucleotides, but is preferably at least 1 nucleotide.

The label-attracting group is preferably attached by means of a spacer, i.e., a bridge consisting of 4 or more atoms. In branched probes, i.e., probes that contain a central primary sequence with numerous branching points and peripheral secondary sequences attached to the branching points, the label-attracting groups can be inserted in either the primary or secondary sequence, or in both sequences.

The method according to the invention works especially well with nucleic acid tests, i.e., when the substance to be analyzed is a nucleic acid. The advantages of the method according to the invention are also obvious in very simple processes such as detecting molecules on a surface, e.g. streptavidin bound to the surface of a tube wall. In this case, the probe is an oligonucleotide that contains a biotin molecule as the analyte-specific portion. The oligonucleotide portion is the nucleic acid-type portion to which two or more label-attracting groups, e.g., digoxigenin, are bound. In this method, a solution that contains the probe in an excessive quantity over the biotin binding sites of streptavidin is filled into the tube with a streptavidin-coated surface. After an incubation step, the excess probe is removed and a conjugate of antibodies to digoxigenin and aequorin is incubated in the tube with the immobilized probe. Then an excess quantity of the conjugate is removed. The reagents required to determine the aequorin label are then added, a triggering step takes place, and the light flash is measured. The intensity of the flash indicates the relative quantity of aequorin and, therefore, of bound probe. This, in turn, indicates the quantity of streptavidin on the surface.

An advantage of the method according to the invention is that the probe can be much smaller than in methods using signal-promoting hybridization zones, yet still retain the same signal intensity. It should be pointed out that the solubility of branched nucleic acids decreases very strongly as size increases. The fact that the probe according to this invention can be much smaller than previous probes while retaining the same number of label-attracting groups results in a higher solubility or—if the molecular size and solubility remain the same—a higher labelling density. It has been shown that the binding ratio of conjugates to the probe can be improved considerably if non-nucleosidic hapten groups and relatively small signal-producing components—and, therefore, conjugates (preferably smaller than 100 KD)—are used, i.e., access to the multiple labels is improved. This is accomplished because less space is occupied than with enzyme (e.g., alkaline phosphatase, β-galactosidase)-labelled detection oligomer probes, and there is a greater degree of conformational freedom. In other words, the proper spacing between hapten and backbone, and between anti-hapten components and signal-producing components of the conjugate results in a more flexible spacial orientation. This makes it easier to quantify the analysis. In addition, with a hybridization immunoassay of this nature—unlike a pure hybridization assay—the label and conjugate incubation takes place at relatively moderate temperatures, e.g., 37° C., which translates into considerable advantages in terms of retaining the specific activity of the conjugate added. In a pure hybridization assay, on the other hand, the requirements for specificity (highest temperature possible) and label activity (low temperature) work against each other. Thermal destruction of conjugate function immediately reduces the level of analytical test sensitivity that can be achieved. The method according to the invention improves multi labelling of the probe. In addition, labels can also be inserted into the primary sequence of the backbone without a significant increase in molecular size using the method according to this invention, in contrast to signal-promoting hybridization zones. The method according to the invention is also suitable for use in therapy monitoring.

BRIEF DESCRIPTION OF THE DRAWINGS

FIG. 1 shows that the nucleic acid to be detected (4) can be bound by means of capture probes (3) to a universal solid phase consisting of a biotinylated capture probe and a (strept)avidin-coated test carrier wall, for instance. As an alternative, a special solid phase probe can be eliminated and the reaction complex can be immobilized directly by means of biotinylated capture probes. The bound nucleic acid to be detected is detected on the solid phase by means of a promoting probe (5) and the probes according to the invention (6). The nucleic acid can bind to the solid phase at numerous sites simultaneously. The probe according to the invention can also bind with the nucleic acid at numerous sites. It is an advantage in this case if just one type of probe is used to detect various nucleic acids. The intermediate probes (5) play a role here that ensure the universal nature of the application. The probe shown in FIG. 1 is constructed of a primary sequence that has 16 branching points and 16 secondary sequences bound to it. Non-nucleosidic, label-attracting groups (7) are inserted into the primary sequence in regions that do not overlap with the branching points. In addition, each of the secondary sequences contains three label-attracting, non-nucleosidic groups. Due to the steric conditions of the probe according to the invention, a virtually stochiometric saturation of the non-nucleosidic, label-attracting groups is facilitated by the binding of conjugates consisting of an antibody directed against the label-attracting group and a calcium-dependent photoprotein.

FIG. 2 shows the steps that take place in a determination procedure for a ribonucleic acid (RNA) from a cell. At the beginning of the procedure, the ribonucleic acid is present in the cell. In an initial step, the cell is broken open (using a known procedure, e.g., lysis using proteases), any RNAses that are present are disintegrated, and the RNA is released. In a subsequent step (B), the oligonucleotides (5), capture probes (3), and the sample that contains RNA are combined in a microtiter plate and incubated. This causes the nucleic acids and probes that were added to bind to the solid phase. Non-bound protein components, excess capture probes, and oligonucleotides (5) are then washed away. In step C, probes according to the invention (6) are incubated in a quantity that exceeds the quantity of bound oligonucleotides expected (5) in conditions in which the universal nucleotide portion of the probe can hybridize with the universal portion of the oligonucleotide (5). An excess of non-bound probes according to the invention is removed in a wash step. In step D the probe molecules that are bound to the solid phase by means of the nucleic acid to be detected and the label-attracting, non-nucleosidic groups located on the probe molecules are occupied when conjugate is added (8) and the mixture is incubated. Excess conjugate is washed away. In step E, the reagents required to detect the signal-producing components are added—with calcium ions as the trigger in this special case. In step F, the light flash that is created (G) is measured and evaluated as a measuring signal—given in relative luminescence units (RLU)—to directly quantify the quantity of nucleic acid to be detected. Since the intensity of the flash signal is directly proportional to the number of bound conjugates and, therefore, the quantity of bound nucleic acids to be detected, the quantity of nucleic acid can be determined directly from the flash intensity.

Figure 1:
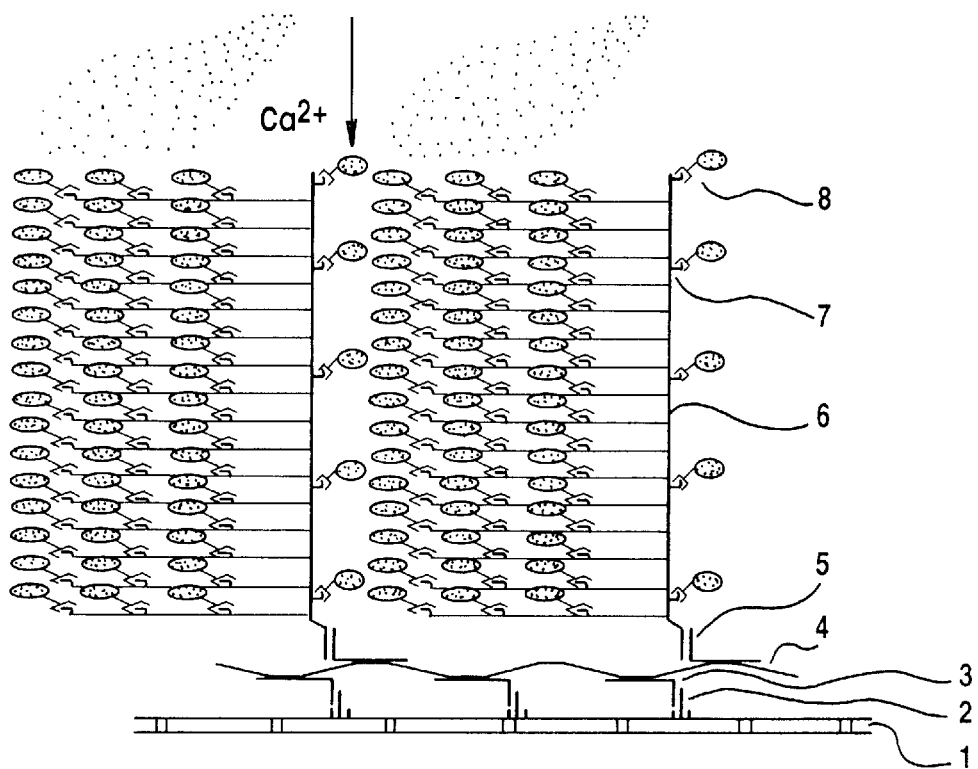
FIG. 1 is an illustration of complex that can be formed in the course of the method according to this invention to detect a nucleic acid.
Figure 2:
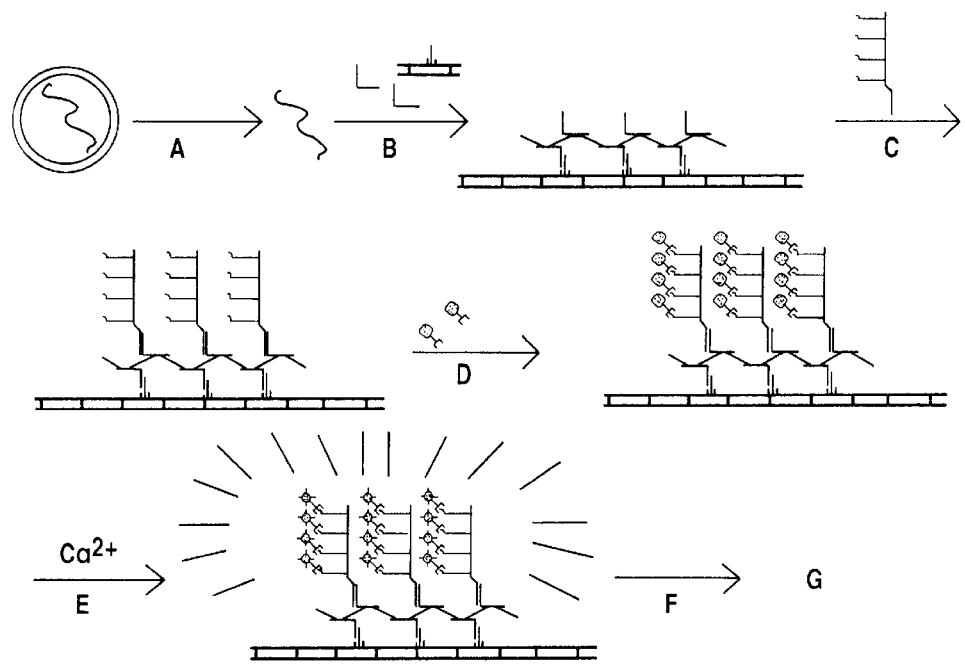
FIG. 2 is an illustration of a method for detecting ribonucleic acids from cells.
Figure 3:
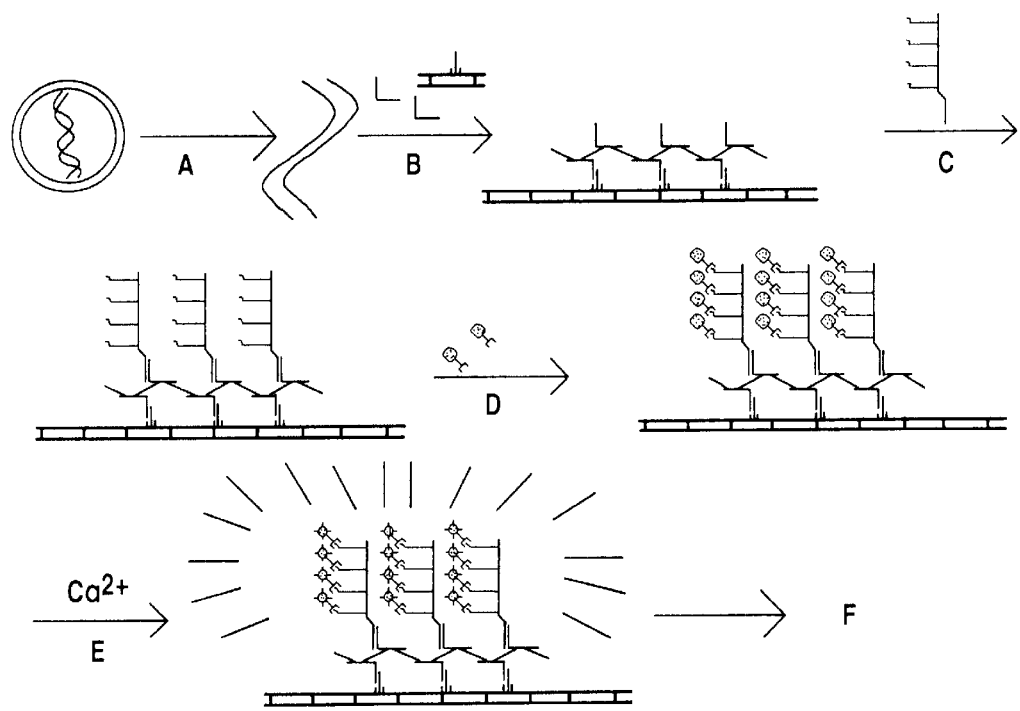
FIG. 3 is an illustration of a method for detecting cellular DNA.

The same procedure is illustrated in FIG. 3, although DNA is used as the nucleic acid to be detected in this case. The cells are first broken open to release the DNA. Step A also includes the denaturing of any double-stranded DNA that may be present. This can take place using a heating step or in alkaline conditions, for instance.

Preferred characteristics of the invention are as follows:
1. The amplification unit does not form during the test via hybridization/aggregation of individual probes, but rather it is a defined, preformed reagent in the sense of a chemical compound with a planned constitution and configuration.
2. No hybridization zones for subsequently added detection probes, but rather low molecular reporter molecules at a distance from each other that is less than the usual length of hybridization zones (16–26 nucleotides), i.e., a high signal intensity is easier to achieve with the same molecular size.
3. Small, flexibly spaced reporter groups are used in conjunction with relatively small conjugates that are also flexibly assembled via linkers, as well as small signal-producing tigger substances with no high molecular additives. This results in a better functionality due to steric advantages in terms of space filling and the spatial orientation.
4. The high density of reporter groups interferes with the potential of the signal-promoting (nucleic acid-like) portion of the probe to (self-) hybridize, i.e., there are no special requirements on the nucleotide sequence or related symmetry characteristics of the signal-producing portion.
5. The invention uses the principle of a hybridization immunoassay, i.e., better retention of the specific activity of the detection reagent.
6. The use of an amplification probe along with a sterically less complex detection system that is inert to DNA and supports a high test sensitivity—not by cyclic, additional signal amplification, but rather by a very high signal/noise ratio, as with the aequorin system—is especially advantageous.
7. The entire technical detection range of the luminometer can therefore be used, i.e., a broad, dynamic measuring range is obtained.

The following examples explain the invention in more detail:

EXAMPLE 1

Synthesis of a Conjugate from a Polyclonal Antibody to Digoxigenin and Aequorin

Place recombinant aequorin (AquaLite™, SeaLite Sciences, Inc.) in a concentration of 2.4 mg/ml in a buffer that has the following composition:

10 mM HEPES, 200 mM NaCl, 2 mM EDTA, 2 mM DTT, pH 8.0

Introduce 1.2 to 1.6 additional SH groups by reacting the mixture with a 15-fold molar excess of 2-iminothiolan (=Traut's reagent) for 30 minutes at 25° C. while stirring. Add L-lysine while stirring for $\geq 15$ minutes at 25° C. to stop the reaction (final concentration: 10 mM). Adjust the buffer of the reaction solution to that of the conjugate buffer and concentrate the solution.

Dissolve an anti-DIG-Fab fragment (obtained from sheep antiserum) purified using affinity chromatography (positive immunosorption) in 30 mM Na phosphate buffer, pH 7.1, in a concentration of $\geq 5$ mg/dl. React this mixture with a 1.3 to 1.7-fold molar excess of MHS (maleinimido-hexanoyl-N-hydroxysuccinimidate) or SMCC (succinimidyl-4-[N-maleimidomethyl]-cyclohexame-1-carboxylate), dissolved in DMSO (stir for 60 minutes at 25° C.). This enables insertion of approximately one MH group per Fab fragment. Add L-lysine while stirring for 30 minutes at 25° C. to stop the reaction (final concentration: 10 mM). Adjust the buffer of the reaction solution to that of the conjugate buffer and concentrate the solution.

The two activated components are then brought into reaction in a coupling ratio of aequorin-SH: Fab-MH=2.5:1 in 25 mM HEPES, 3 mM EDTA, pH 7.5. The concentration of aequorin-SH is approximately 1 mg/ml. Allow the reaction to take place for 60 minutes at 25° C. while stirring. Add cysteine or dithiothreitol (final concentration of 2 mM or 5 mM, respectively) to stop the reaction.

The <DIG>-Fab-aequorin conjugate produced is then purified by a combination of separation by charge (ion exchange column, Q Sepharose FF or DEAE 5PW) and separation by molecular size (gel filtration column, Sephacryl S 200-HR). It is then concentrated to a small volume, aliquotted, and stored in a HEPES storage buffer at −70° C.

The sequence of separation steps can be reversed.

To perform the tests, thaw the aliquots, dilute them in test buffer to working solution concentration, and use them on the same day.

EXAMPLE 2

Manufacture of an Unbranched Probe According to the Invention (TDN)

Manufacture of an oligonucleotide having the formula

5'-X TTT TTT TAT AYG GGC ATY TGG TGG Y (SEQ ID NO 1)

with X=biotin hexapropanolphosphate and Y=3-amino-1,2-propandiol phosphate, whereby Y is subsequently labelled with digoxigenin-3-O-methyl-carbonyl-6-amino caproic acid-N-hydroxy-succinimide ester. The synthesis is performed on a Gene Assembler Plus from Pharmacia according to the standard protocols in the user instructions. The nucleotide components used are standard phosphoramidite 5'-dimethoxytrityl-N-benzoyl-2'-deoxy adenosine, 3'-[(2-cyanoethyl)-(N,N-diisopropyl)]-phosphoramidite, 5'-dimethoxytrityl-N-benzoyl-2'-desoxy cytidine, 3'-[(2-cyanoethyl)-(N,N-diisopropyl)]-phosphoramidite, 5'-dimethoxytrityl-N-isobutyryl-2'-desoxy guanosine, 3'-[(2-cyanoethyl)-(N,N-diisopropyl)]-phosphoramidite and 5'-dimethoxytrityl-2'-desoxy tymidine, [(2-cyanoethyl)-(N,N-diisopropyl)]-phosphoramidite (from ABI). Biotin phosphoramidite (ABI 401395) is used in the x position, and 9-fluorenyl-methoxycarbonayl-3-amino-1-di-methoxytrityl-2-propandiol-[(2-cyanoethyl)-(N,N-diisipropyl)]- phosphoramidite is used in the y position. The quantity synthesized is 1.3 $\mu$mol on a 5'-dimethoxytrityl-2'-desoxy thymidine 3-succinoyl long chain alkylamino-controlled pore glass carrier. After 20 hours at 37° C. in a 32% ammonia solution, the oligonucleotide is separated from the carrier and, at the same time, the $\beta$-cyanoethyl groups and protective groups of the free amino groups are separated. The raw product is purified via HPLC (Lichrosorb RP 18.8×250 mm, from CS—Chromatography Service) using a 0.1 m triethyl ammonium acetate/ acetonitrile gradient, and desalted using dialysis. After the solvent is removed in a vacuum, the oligonucleotide is labelled according to the Boehringer Mannheim protocol (EP-0 371 262) using the digoxigenin-3-O-methyl carbonyl-5-amino caproic acid-N-hydroxy-succinimide ester. After the labelling reaction, the oligonucleotide is dialyzed, concentrated, and purified via chromatography (HPLC Lichrosorb RP 18.8×250 mm, CS—Chromatography Service) using a 0.1 M triethyl ammonium acetate/acetonitrile gradient, then desalted using dialysis. The digoxigenin label is detected as described by Gebeyechu, G., et al. (1987), Nucl. Acids Res. 15, 4513.

EXAMPLE 3

Detection of streptavidin on a microtiter plate using the method according to the invention and comparison with single-labelled probes
Test sensitivity with anti-DIG-fab-aequorin-conjugate

Figure 4:
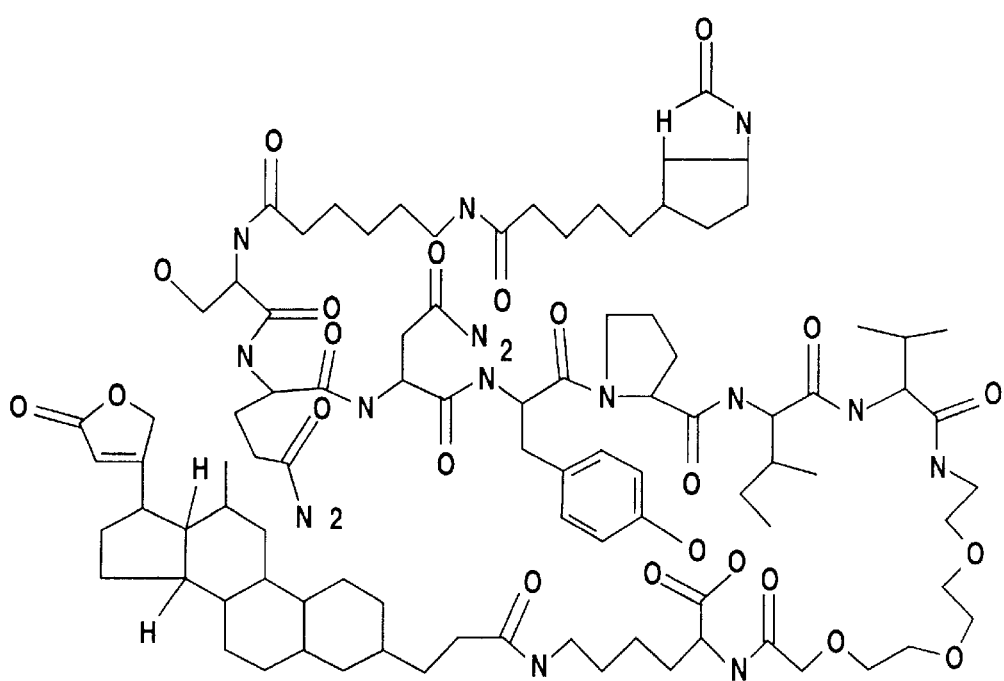
FIG. 4 is an illustration of the structure of a peptide (MDP) used in the examples.

| | |
|---|---|
| Test carrier: | white microtiter plates from Nunc, MaxiSorb type, coated with tBSA-SA (thermo BSA streptavidin) by MicroCoat |
| Volume: | 25 $\mu$l DIG reagent (mono-biotin-mono-digoxigenin-heptapeptide, FIG. 4, (MDP), in various concentrations) + 50 $\mu$l <DIG> -aequorin conjugate from Example 1 in test buffer (approx. 4 × 10$^6$ RLU/test) |
| Test format: | 15 min simultaneous incubation (1-step assay) |
| B/f separation: | SLT plate washer SW 812 A2, prog. 2 (= wash 4 times) |
| Test buffer: | 25 mM HEPES, 150 mM KCl, 10 mM EGTA, 2 mg/ml BSA, 1.5 mg/ml BSA-c, 0.05% (v/v) Tween 20, 0.1% (w/v) NaN$_3$, pH 7.0 |
| Measurement device: | Dynatech ML 3000 plate reader, peak mode (0.1 sec before peak + 2.0 sec after peak) |

| pmol/l DIG reagent | Bound signal [RLU] (mean ± SD) | | Slope (S/N) |
|---|---|---|---|
| 0.0 | 3346 | +457 | 2.71 |
| 0.2 | 9079 | | 15.96 |
| 2.0 | 53405 | | 182.86 |
| 20.0 | 611900 | | 1581.00 |
| 200.0 | 5290000 | | 7890.00 |
| 1000.0 | 26400000 | | | lower detection limit* = 0.032 pmol/l = 8 × 10$^{-19}$ mol/well = approx. 4.8 × 10$^5$ molecules of substance to be analyzed
*calculated based on zero value + 2-fold standard deviation from replicate measurements at zero dose.

EXAMPLE 4

Comparative evaluation of mono-biotin-mono-digoxigenin-heptapeptide (MDP) vs. mono- 5'-biotin-tri-digoxigenin-28 mer-oligonucleotide (TDN)

| | |
|---|---|
| Test carrier: | white microtiter plates from Nunc, MaxiSorb type, coated with tBSA-SA (thermo BSA streptavidin) by MicroCoat |
| Volume: | 25 µl DIG reagent (mono-biotin-mono-digoxigenin-heptapeptide in various concentrations) + 50 µl <DIG>-aequorin conjugate from Example 1 in test buffer (approx. 4 × 10⁶ RLU/test) |
| Test format: | 15 min simultaneous incubation (1-step assay) |
| B/f separation: | SLT plate washer SW 812 A2, prog. 2 (= wash 4 times) |
| Test buffer: | 25 mM HEPES, 150 mM KCl, 10 mM EGTA, 2 mg/ml BSA, 1.5 mg/ml BSA-c, 0.05% (v/v) Tween 20, 0.1% (w/v) NaN₃, pH 7.0 |
| Measurement device: | Dynatech ML 3000 plate reader, integration mode |

| Bound signal DIG Reagent | [RLU]-TDN | | [RLU]-TDN | | Factor |
|---|---|---|---|---|---|
| [pmol/l] | Exp. 1 | Exp. 2 | Exp. 1 | Exp. 2 | TDN/MDP |
| 0.0 | 378 | 383 | 143 | 119 | |
| | (170 | 182) | (200 | 196) | |
| 0.1 | 498 | 473 | 109 | 115 | |
| 1.0 | 1075 | 1150 | 323 | 289 | 3.33 |
| | | | | | 3.99 |
| 10.0 | 7055 | 7150 | 1895 | 1935 | 3.72 |
| | | | | | 3.70 |
| 100.0 | 60850 | 54350 | 19550 | 19250 | 3.11 |
| | | | | | 2.82 |

EXAMPLE 5

Synthesis of a Branched Oligonucleotide

Figures 5, 6, 7, 8, 9:
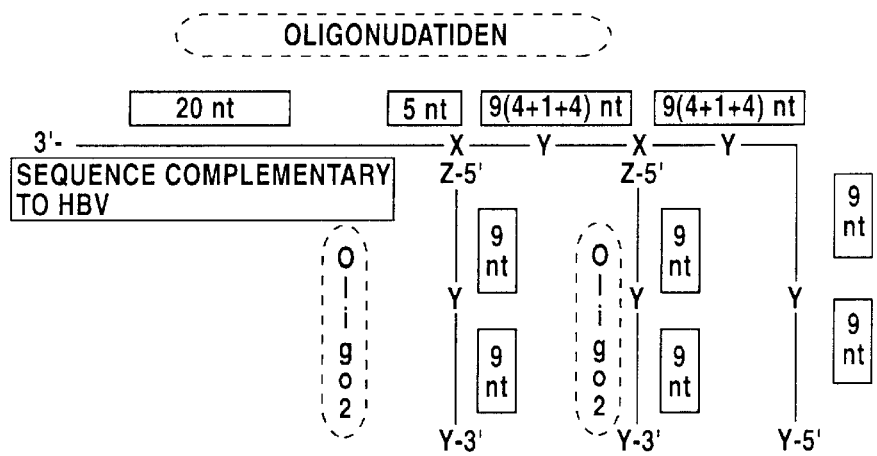
FIG. 5 is a schematic representation of the construction of oligonucleotide 1, a branched oligonucleotide according to the present invention.
FIGS. 6–11 are lists of the sequence of additional oligonucleotides that can be used either as intermediate or end products according to the present invention.

Reference is made to the figures (FIG. 5–12) as an explanation of this example. In FIG. 5, X refers to branching points via 3-amino-1,2-propandiol phosphate. Y refers to DNP-TEG-phosphoramidite label sites. Z refers to mercaptohexyl linking sites.

1. Oligonucleotide Synthesis

Refer to the sequence protocols for the sequences of single-stranded and linear oligonucleotides. Refer to the figures for the sequences of the single-stranded but branched oligonucleotides. Synthesis is performed on a Gene Assembler Plus from Pharmacia based on the standard protocols of the user instructions and the data provided by the phosphoramidite manufacturer.

The following standard phosphoramidites are used as nucleotide components:
5'-dimethyoxytrityl-N-benzoyl-2'-deoxy adenosine, 3'-[(2-cyanoethyl)-(N,N-diisopropyl)]-phosphoramidite, 5'-dimethoxytrityl-N-benzoyl-2'-desoxy cytidine, 3'-{(cyanoethyl)-(N,N-diisopropyl)]-phosphoramidite, 5'-dimethoxytrityl-N-isobutyryl-2'-desoxy guanosine, 3'-[(2-cyanoethyl)]-(N,N-diisopropyl)]-phosphoramidite, and 5'-dimethoxytrityl-2'-desoxy thymidine, [(2-cyanoethyl)-(N, N-diisopropyl)]-phosphoramidite (from ABI). The following is used in the X position for branching: 3-[N-(9-fluorenylmethoxycarbonyl)-6-amino capronic acid]-amino-1-(4,4'-dimethoxytrityl)-1,2-propandiol-2-[(2-cyanoethyl)-(N,N-diiso-propyl)] phosphoramidite. The following is used as the label in the Y position: DNP-TEG-phosphoramidite (FIG. 12, Glen Research 10–1985. Refer also to: Nucleic Acids Research 21, 1993, 1705–1712). The following is used in the Z position for linking: 5'-thiol modifier C6 (Glen Research 10–1926). The quantity of oligonucleotide synthesized is 1.3 □mol on a 5'-dimethoxytrityl-2'-desoxy thymidine 3'-succinoyl long chain alkyl amino-controlled pore glass carrier. After 5 hours at 55° C. in a 32% ammonia solution, the oligonucleotides are separated from the carrier and, simultaneously, the β-cyanoethyl groups and base-labile amino protective groups are separated. The raw products are purified using HPLC (Lichrosorb RP 18, 8×250 mm, from CS—Chromatography Service) using a 0.1 M triethylammonium acetate/acetonitrile gradient, then desalted using dialysis. The thiol group protection of the oligonucleotide 2 is removed per the Glen Research User Guide, extracted 5 times with acetic acid, and then lyophilized in a Speedvac.

Oligonucleotide 1 XDNP (=1 Xlin), 2XDNP (=2X lin), and 2X'DNP (=2'Xlin), and oligonucleotides 1 and 2 were synthesized separately according to these specifications.

2. Maleinimido Functionalization of Oligonucleotide 1

Dissolve lyophilized oligonucleotide 1 in 350 µl sodium hydrogen carbonate buffer, 0.1 mol/l, pH 8.5. Add a solution of 1 mg maleinimido-hexyl-N-hydroxy succinimide ester in 50 µl acetonitrile. Shake the reaction solution overnight in a thermal mixer at 20° C. Separate the oligonucleotide from free maleinimide and salt using a NAP-25 column (Pharmacia), then concentrate it and purify it using chromatography (HPLC Lichrosorb RP 18.8×250 mm, CS—Chromatography Service) using a 0.1 M triethyl ammonium acetate/acetonitrile gradient. Desalt the preparation by dialysis.

3. Linking Reaction of Oligonucleotides 1 and 2

Dissolve 10 OD of oligonucleotide 1 in 50 µl 0.1 phosphate buffer pH 6.0 and add it to 30 OD oligonucleotide 2. Shake the reaction mixer for 3 days in a thermal mixer at 20° C. Perform the purification using an 8% preparative polyacrylamide gel. In this step, educt oligonucleotides and, in particular, the 6XDNP intermediate product (=6X bNA) are separated from the 8XDNP oligonucleotide (=8X bNA)

desired. The 6XDNP oligonucleotide results from a mere one-fold coupling of oligonucleotide 2 to oligonucleotide 1. The yield is 6.6 OD 8XDNP oligonucleotide and 4.8 OD 6XDNP oligonucleotide. The purity was determined using HPLC (RP 18 Hypersil ODS 4.5×250 mm from CS—Chromatography Service) using a 0.1 M triethyl ammonium acetate/acetonitrile gradient.

EXAMPLE 6

Hybridization Immunoassay with DNP-labelled Indicator Probes

Figures 10, 11, 12:
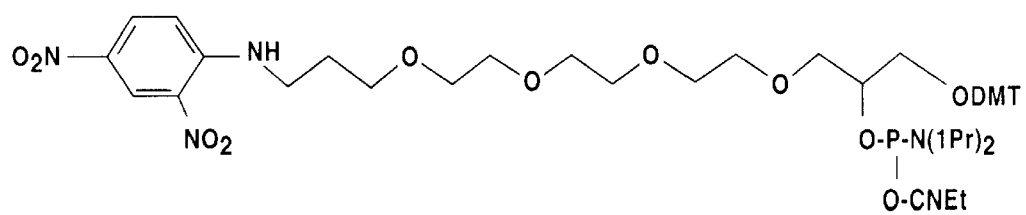
FIG. 12 is an illustration of the structure of a reagent used in the examples for inserting the label groups.
Figure 13:
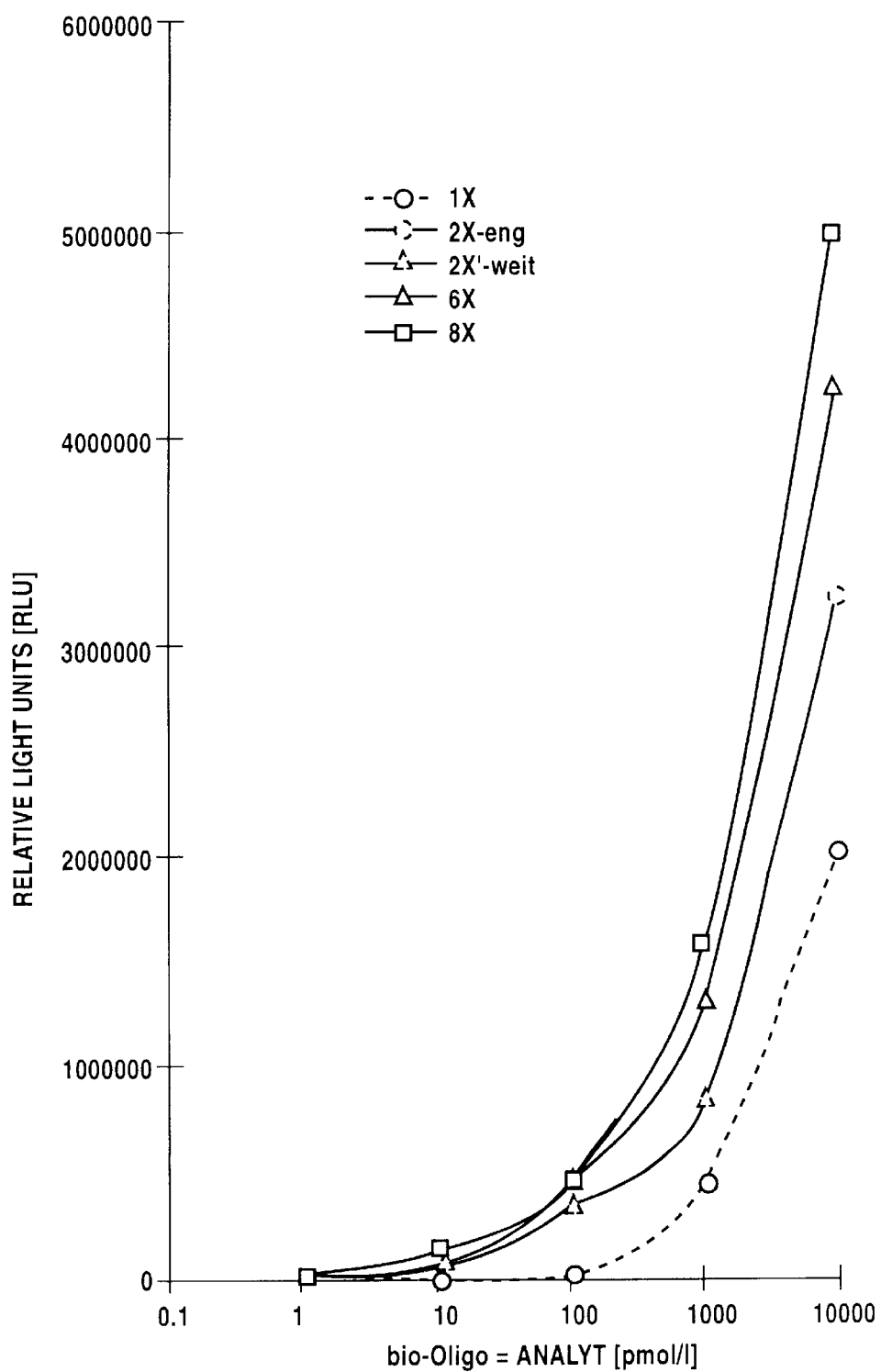
FIG. 13 is an illustration of comparative signal measurements for the oligonucleotides made and used in the method to detect nucleic acids.

The indicator probes described in Example 5 were tested in hybridization immunoassays for comparison purposes. Explanations:

- 1X lin=linear 31-mer DNA oligo with a 5'-terminal DNP label and a 20 nt sequence 3'-terminal that is complementary to the HBV oligo #33-1 (FIG. 7).
- 2X lin (also 2Xeng (2Xnarrow) in FIG. 13)=linear 41-mer DNA oligo with two DNP labels (pos. 1 and 11, 5'→3', i.e., separated from each other by means of a 9 nt spacer), and a 20 nt sequence 3'-terminal that is complementary to the HBV-oligo #33-1.
- 2X' lin (also 2Xweit (2Xbroad) in FIG. 13)=linear 51-mer DNA oligo with two DNP labels (pos. 1 and 21, 5'→3', i.e., separated by means of a 19 nt spacer), and a 20 nt sequence 3'-terminal that is complementary to the HBV-oligo #33-1.
- 6X bNA=branched 83-mer DNA oligo with a total of 6 DNP labels, 2 in the stem sequence and 2 in each of the two branch sequences, according to FIG. 10.
- 8X bNA=branched 104-mer DNA oligo with a total of 8 DNP labels, 2 in the stem sequence and 2 in each of the three branch sequences, according to FIG. 11.

Various concentrations of a 5'-biotinylated 20 nt oligomer that is complementary to an HBV wild type sequence were used as the immobilization reagent and, at the same time, the substance to be detected.

Test Format:

- Test carrier: white MaxiSorp™ microtiter plates from Nunc, SA-coated. Or, white, uncoated MicroLite™ microtiter plates from Dynatech.
- Immobilization: by means of 20 nt-oligo-5'-biotin (FIG. 7) in a concentration range of 0.1–10,000 pmol/l, which also functions as the substance to be detected.
- Test buffer for hybridization experiments
  25 mM Hepes pH 7.4
  150 mM NaCl
  10 mM EGTA
  0.5% (w/v) BSA
  0.5% (w/v) Tween-20
  0.1% $NaN_3$
  Optional additional additive of 0.15 (v/v) BSA-c (a partially linearized and acetylated BSA preparation from Aurion/The Netherlands) or 200 mM $Na_2$-tartrate x $2H_2O$
- Test format: 3-step delayed solid phase assay
- Test steps: perform solution hybridization with 20 nt-oligo-biotin and one each of the DNP-labelled indicator probes described for 60 minutes at RT while shaking in uncoated microtiter plates. Transfer the preparation to SA-coated microtiter plates using a multichannel pipette. Incubate for 15 minutes at room temperature while shaking to facilitate immobilization by means of the SA-biotin interaction. Wash (i.e., separate solid phase-bound and unbound reaction complexes), then incubate for 30 minutes at room temperature while shaking to facilitate reaction of the solid phase-bound hybridization complexes with a MAb<DNP>M-Fab-aequorin conjugate (made like the <DIG>-aequorin described in Example 1). Wash again, then measure the aequorin bioluminescence. The signal strength is directly proportional to the analyte concentration.

Reaction volume: 50 μl 20 nt oligo-5'-biotin (=analyte)+ 50 μl indicator probe. Transfer 50 μl reaction solution per well; 50 μl conjugate.

Wash module: SLT Columbus Plate Washer

Measurement module: Dynatech ML 3000 Plate Luminometer

Trigger: 10 mM Tris, pH 7.4, with 100 mM $CaCl_2$

Measurement mode: integrated flash mode, 0.1 sec before peak and +1.0 sec after peak; gain high

EXAMPLE 6A

A concentration range of 0–1000 pmol/l was measured for 20 nt-HBV-oligo-5'-biotin under the test conditions described. The DNP-labelled probes were used in a concentration of 10 nmol/l, and the <DNP> aequorin conjugate was used in a concentration of approx. $1 \times 10^6$ RLU/test. The results are shown in Table 1.

TABLE 1

DNA hybridization immunoassay with DNP-labelled indicator probes

| Analyte = 20 nt-oligo-5'-biotin | Bound signals [RLU] | | | | |
|---|---|---|---|---|---|
| [pmol/l] | 1 X lin | 2 X lin | 2 X'lin | 6 X bNA | 8 X bNA |
| 0 | 3.38 E + 03 | 5.27 E + 03 | 4.02 E + 03 | 9.13 E + 03 | 1.58 E + 04 |
| 1 | 3.78 E + 03 | 2.26 E + 04 | 2.17 E + 04 | 3.84 E + 04 | 6.39 E + 04 |
| 10 | 4.52 E + 03 | 8.83 E + 04 | 8.43 E + 04 | 1.36 E + 05 | 1.91 E + 05 |
| 100 | 4.51 E + 04 | 3.58 E + 05 | 4.23 E + 05 | 4.95 E + 05 | 5.46 E + 05 |
| 500 | 3.62 E + 05 | 7.06 E + 05 | 6.90 E + 05 | 1.07 E + 06 | 1.28 E + 06 |
| 1000 | 5.51 E + 05 | 8.82 E + 05 | 1.00 E + 06 | 1.59 E + 06 | 1.85 E + 06 |

The resulting dose-response characteristics are:

| Analyte = 20 nt-oligo- | Bound signals [RLU] | | | | |
|---|---|---|---|---|---|
| 5'-biotin [pmol/l] | 1X lin | 2X lin | 2X' lin | 6X bNA | 8X bNA |
| Signal quotients (increase in dynamics) standardized to 1X lin | | | | | |
| 0 | 1.00 | 1.56 | 1.19 | 2.70 | 4.67 |
| 1 | 1.00 | 5.98 | 5.74 | 10.16 | 16.90 |
| 10 | 1.00 | 19.54 | 18.65 | 30.09 | 42.26 |
| 100 | 1.00 | 7.94 | 9.38 | 10.98 | 12.11 |
| 500 | 1.00 | 1.95 | 1.91 | 2.96 | 3.54 |
| 1000 | 1.00 | 1.60 | 1.81 | 2.89 | 3.36 |
| Absolute signal increases, based on 1X lin | | | | | |
| 0 | | 1.89E+03 | 6.40E+02 | 5.75E+03 | 1.24E+04 |
| 1 | | 1.88E+04 | 1.79E+04 | 3.46E+04 | 6.01E+04 |
| 10 | | 8.38E+04 | 7.98E+04 | 1.31E+05 | 1.86E+05 |
| 100 | | 3.13E+05 | 3.78E+05 | 4.50E+05 | 5.01E+05 |
| 500 | | 3.44E+05 | 3.28E+05 | 7.08E+05 | 9.18E+05 |
| 1000 | | 3.31E+05 | 4.49E+05 | 1.04E+06 | 1.30E+06 |

Non-specific binding increases moderately with increasing DNP insertion. In particular, however, there is an enormous increase in specific binding as a function of the strength of the DNP label, especially in the lower concentration range. The higher the DNP insertion, the better the slope of the curve. In other words: with the signal amplification according to the invention, it is much easier to differentiate small analyte concentrations from "zero". This is verified by the signal quotients and the absolute signal increases relative to 1X lin.

This is supported by calculating the corresponding analytical sensitivity using linear regression between 0–10 pmol/l based on two-fold standard deviation from the mean of a quadruplicate determination of the zero value.

| | Slope 0–10 pM [RLU] | Zero value precision [% Cv] | Detection limit [pmol/l] |
|---|---|---|---|
| 1 X lin | 1140 | 11.23 | 6.65 |
| 2 X lin | 83030 | 16.23 | 0.21 |
| 2 X' lin | 80280 | 40.01 | 0.40 |
| 6 X bNA | 126876 | 2.83 | 0.04 |
| 8 X bNA | 175200 | 9.30 | 0.167 |

The exceptionally positive detection limit at 6X bNA is due to the extremely good zero value precision in this case. In general, detection limit=$f^1$ (X DNP).

Table 1 also illustrates that the elevated specific signal generation serves as a function of the strength of DNP label across the entire calibration curve.

The concept according to the invention is also confirmed by the fact that specific bindings with 2X lin and 2X' lin probes do not differ significantly from each other, i.e., 2 hapten labels (by reacting with MAb<DNP>Fab aequorin) lead to an almost identical signal increase as compared with 1X lin, regardless of whether the two labels are separated (9 nt or 19 nt) from each other. In other words: very close label sites as compared with the prior art are realized by flexibly spacing the hapten labels (in this case: the 3-amino propyl-triethylene glycol-glyceryl spacer in the DNP-TEG) and the sterically little demanding anti-hapten conjugate (in this case: <DNP>Fab-aequorin [1:1], M, approx. 70 kD, flexibly linked using a 14 atom linker).

EXAMPLE 6B

Test performed as described in Example 6A, but with a measuring range extended by a factor of 10, to 10,000 pmol/l, and using 0.15% BSA-c in the conjugate dilution buffer.

Once more, the results (see Table 2) confirm the concept according to the invention in two ways:

2X lin and 2X' lin probes cannot be distinguished from each other with regard to generating specific binding, i.e., a high label density can be fully realized specific binding is precisely a function of the number of DNP labels inserted, i.e., a plurality of label sites can be fully realized.

TABLE 2

DNA hybridization immunoassay with DNP-labelled indicator probes

| Analyte = 20 nt-oligo- 5'-biotin | Bound signals [RLU] | | | | |
|---|---|---|---|---|---|
| [pmol/l] | 1 X lin | 2 X lin | 2 X' lin | 6 X bNA | 8 X bNA |
| 0 | 4.38 E + 03 | 6.47 E + 03 | 4.76 E + 03 | 7.82 E + 03 | 1.45 E + 04 |
| 1 | 4.07 E + 03 | 1.12 E + 04 | 1.26 E + 04 | 1.89 E + 04 | 3.02 E + 04 |
| 10 | 5.67 E + 03 | 7.05 E + 04 | 7.49 E + 04 | 9.68 E + 04 | 1.53 E + 05 |
| 100 | 3.98 E + 04 | 3.57 E + 05 | 3.63 E + 05 | 4.78 E + 05 | 4.87 E + 05 |
| 500 | 4.78 E + 05 | 8.36 E + −5 | 8.72 E + 05 | 1.34 E + 06 | 1.6 E + 06 |
| 1000 | 2.05 E + 06 | 3.26 E + 06 | 3.26 E + 06 | 4.27 E + 06 | 5.02 E + 06 |

The resulting dose-response characteristics are:

| Analyte = 20 nt-oligo- | Bound signals [RLU] | | | | |
|---|---|---|---|---|---|
| 5'-biotin [pmol/l] | 1X lin | 2X lin | 2X' lin | 6X bNA | 8X bNA |
| Signal quotients (increase in dynamics) standardized to 1X lin | | | | | |
| 0 | 1 | 1.48 | 1.09 | 1.79 | 3.31 |
| 1 | 1 | 2.75 | 3.10 | 4.64 | 7.42 |
| 10 | 1 | 13.91 | 14.77 | 19.09 | 30.18 |
| 100 | 1 | 8.97 | 9.12 | 12.01 | 12.24 |
| 500 | 1 | 1.75 | 1.82 | 2.80 | 3.37 |
| 1000 | 1 | 1.59 | 1.60 | 2.08 | 2.45 |
| Absolute signal increases, based on 1X lin | | | | | |
| 0 | | 2.09E+03 | 3.80E+02 | 3.44E+03 | 1.01E+04 |
| 1 | | 7.13E+03 | 8.53E+03 | 1.48E+04 | 2.61E+04 |
| 10 | | 6.54E+04 | 6.98E+04 | 9.17E+04 | 1.48E+05 |
| 100 | | 3.17E+05 | 3.23E+05 | 4.38E+05 | 4.47E+05 |
| 500 | | 3.58E+05 | 3.94E+05 | 8.62E+05 | 1.13E+06 |
| 1000 | | 1.21E+06 | 1.23E+06 | 2.22E+06 | 2.97E+06 |

EXAMPLE 6C

The measuring range in this case was 0–1000 pmol/l. To reduce the amount of non-specific binding, 200 mM $Na_2$ tartrate x $2H_2O$ was added to the test buffer (→salt-rich buffer environment) and the DNP probe concentration was reduced to 5 nmol/l. In fact, the non-specific binding was more than halved. Compared with specific binding, the results described earlier and, therefore, the concept according to the invention, were confirmed once more. Reference is made to Table 3.

TABLE 3

DNA-hybridization immunoassay with DNP-labelled indicator probes

| Analyte = 20 nt-oligo-5'-biotin | Bound signals [RLU] | | | | |
|---|---|---|---|---|---|
| [pmol/l] | 1 X lin | 2 Xlin | 2 X'lin | 6 X bNA | 8 X bNA |
| 0 | 3.72 E + 03 | 2.54 E + 03 | 4.02 E + 03 | 4.58 E + 03 | 6.86 E + 03 |
| 1 | 2.65 E + 03 | 7.54 E + 03 | 6.88 E + 03 | 1.04 E + 04 | 1.54 E + 04 |
| 10 | 2.72 E + 04 | 4.04 E + 04 | 3.66 E + 04 | 6.25 E + 04 | 9.66 E + 04 |
| 100 | 5.79 E + 04 | 1.56 E + 05 | 1.72 E + 05 | 2.50 E + 05 | 3.17 E + 05 |
| 500 | 1.49 E + 04 | 2.37 E + 05 | 2.59 E + 05 | 3.74 E + 05 | 3.93 E + 05 |
| 1000 | 3.12 E + 05 | 5.85 E + 05 | 6.25 E + 05 | 8.35 E + 05 | 9.29 E + 05 |

The resulting dose-response characteristics are:

| Analyte = 20 nt-oligo- | Bound signals [RLU] | | | | |
|---|---|---|---|---|---|
| 5'-biotin [pmol/l] | 1X lin | 2X lin | 2X' lin | 6X bNA | 8X bNA |
| Signal quotients (increase in dynamics) standardized to 1X lin | | | | | |
| 00 | 1 | 0.93 | 1.48 | 1.68 | 2.52 |
| 1 | 1 | 2.85 | 2.60 | 3.92 | 5.81 |
| 10 | 1 | 14.85 | 13.46 | 22.98 | 35.50 |
| 100 | 1 | 26.94 | 29.71 | 43.18 | 54.66 |
| 500 | 1 | 15.91 | 17.38 | 25.10 | 26.34 |
| 1000 | 1 | 1.88 | 2.00 | 2.68 | 2.98 |
| Absolute signal increases, based on 1X lin | | | | | |
| 0 | | −1.80E+02 | 1.30E+03 | 1.86E+03 | 4.14E+03 |
| 1 | | 4.89E+03 | 4.23E+03 | 7.75E+03 | 1.28E+04 |
| 10 | | 3.77E+04 | 3.39E+04 | 5.98E+04 | .38E+04 |
| 100 | | 1.50E+05 | 1.66E+05 | 2.44E+05 | 3.11E+05 |

-continued

| Analyte = 20 nt-oligo- | Bound signals [RLU] | | | | |
|---|---|---|---|---|---|
| 5'-biotin [pmol/l] | 1X lin | 2X lin | 2X' lin | 6X bNA | 8X bNA |
| 500 | | 2.22E+05 | 2.44E+05 | 3.59E+05 | 3.78E+05 |
| 1000 | | 2.73E+05 | 3.13E+05 | 5.23E+05 | 6.17E+05 |

EXAMPLE 6D

Test performed as described in Example 6C, but using reagents stored at +2–8° C. for 4 days, and 10 nM indicator probe each (diluted from the 100 nM predilection which was also stored at +2–8° for 4 days from which the 5 nM reagent solution in Example 6C was made).

The results are presented in Table 4.

TABLE 4

DNA hybridization immunoassay with DNP-labelled indicator probes

| Analyte = 20 nt-oligo- 5'-biotin | Bound signals [RLU] | | | | |
|---|---|---|---|---|---|
| [pmol/l] | 1 X lin | 2 Xlin | 2 X'lin | 6 X bNA | 8 X bNA |
| 0 | 1.85 E + 03 | 2.36 E + 03 | 1.23 E + 03 | 1.33 E + 03 | 4.94 E + 03 |
| 1 | 2.17 E + 03 | 4.27 E + 03 | 3.26 E + 03 | 6.00 E + 03 | 7.96 E + 03 |
| 10 | 2.38 E + 03 | 1.16 E + 04 | 1.21 E + 04 | 2.00 E + 04 | 2.75 E + 04 |
| 100 | 2.94 E + 03 | 4.49 E + 04 | 4.81 E + 04 | 9.49 E + 04 | 1.28 E + 05 |
| 500 | 3.41 E + 03 | 7.83 E + 04 | 8.90 E + 04 | 1.69 E + 05 | 2.07 E + 05 |
| 1000 | 1.00 E + 05 | 3.63 E + 05 | 3.33 E + 05 | 5.42 E + 05 | 5.42 E + 05 |

The resulting dose-response characteristics are:

| Analyte = 20 nt-oligo- | Bound signals [RLU] | | | | |
|---|---|---|---|---|---|
| 5'-biotin [pmol/l] | 1X lin | 2X lin | 2X' lin | 6X bNA | 8X bNA |
| Signal quotients (increase in dynamics) standardized to 1X lin | | | | | |
| 0 | 1 | 1.28 | 0.66 | 0.72 | 2.67 |
| 1 | 1 | 1.97 | 1.50 | 2.76 | 3.67 |
| 10 | 1 | 4.87 | 5.08 | 8.40 | 11.55 |
| 100 | 1 | 15.27 | 16.36 | 32.28 | 43.54 |
| 500 | 1 | 22.96 | 26.10 | 49.56 | 60.70 |
| 1000 | 1 | 3.63 | 3.33 | 5.24 | 5.42 |
| Absolute signal increases, based on 1X lin | | | | | |
| 0 | | 5.10E+02 | −6.20E+02 | −5.20E+02 | 3.09E+03 |
| 1 | | 2.10E+03 | 1.09E+03 | 3.83E+03 | 5.79E+03 |
| 10 | | 9.22E+03 | 9.72E+03 | 1.76E+04 | 2.51E+04 |
| 100 | | 4.20E+04 | 4.52E+04 | 9.20E+04 | 1.25E+05 |
| 500 | | 7.49E+04 | 8.56E+04 | 1.66E+05 | 2.04E+05 |
| 1000 | | 2.63E+05 | 2.33E+05 | 4.24E+05 | 4.42E+05 |

Conclusion: Multiple labels using haptens and a high label density do not decrease stability in solution. Rather, the opposite is true. In other words: the stability of the product is not affected when the concept of signal amplification according to the invention is used.

| Maximum specific binding (1000 pmol/l analyte) | |
|---|---|
| 1 X lin | 32% recovery relative to example 6C (= fresh) |
| 2 X lin | 62% |
| 2 X' lin | 53% |
| 6 X bNA | 62% |
| 8 X bNA | 60% |

In this case as well—where stressed reagents are used—the advantage of signal amplification according to the invention is clearly demonstrated using signal quotients and signal increases (note in particular the increases at the transition from 6X bNA to 8X bNA), and by using detection limit calculations (similar to Example 6A) in which the zero value precision is weighted over the slope of the curve:

| | analytical sensitivity = detection limit [pmol/l] |
|---|---|
| 1 X lin | 21.80 |
| 2 X lin | 0.89 |
| 8 X bNA | 0.39 |

| Abbreviations: | |
|---|---|
| DNP | dinitrophenyl |
| HBV | hepatitis B virus |
| SA | streptavidin |
| BSA | bovine serum albumin |
| RT | room temperature |
| MAb<X> | monoclonal antibody against X |
| DIG | digoxigenin |
| RLU | relative light units |
| CV | coefficient of variation |

List of Illustrations

1. Bottom or wall of a microtiter plate
2. Active solid phase consisting of a (strept)avidin coating of the test carrier wall, plus a biotinylated solid phase immobilized on it, the sequence of which is complementary to a partial sequence of the capture probe (3).
3. Capture probe with a partial nucleotide sequence that is complementary to the nucleic acid to be detected, and a partial sequence that is complementary to the solid phase probe.
4. Nucleic acid to be detected.
5. Oligonucleotide containing a part that is complementary to part of the nucleic acid to be detected and a universal portion that is complementary to part of the probe that contains the nucleobases (6).
6. Probe according to the invention with comb-like lateral arms projecting from a basic stem.
7. Non-nucleosidic label-attracting group (e.g., digoxigenin) bound to the primary sequence or secondary sequences.
8. Conjugate of a binding partner of the non-nucleosidic, label-attracting group and a calcium-dependent photoprotein (e.g., antidigoxigenin aequorin).

What is claimed is:

1. A method of detecting a substance in a sample, comprising (1) contacting the sample with a probe under conditions in which said substance if present binds directly or indirectly to the probe, which probe comprises a stem and at least one branch, said stem and said at least one branch comprising
a plurality of nucleobases and
at least two non-nucleosidic label-attracting groups, to produce a binding product, wherein said label-attracting groups are groups detectable directly or indirectly;

(2)
(a) mixing the binding product with a conjugate, wherein the conjugate has a molecular weight of no more than 100 kDa and comprises a signal-producing component and a group that has an affinity for the label-attracting group to produce a mixture containing a conjugate-bound binding product;

(b) removing unbound conjugate from said mixture;
(c) determining the presence of the conjugate-bound binding product in said mixture by means of said signal-producing component; and
(d) using the presence of the conjugate-bound binding product as an indication of the presence of the binding product; and thereafter (3) using the presence of the binding product as an indication of the presence of said substance,
wherein the label-attracting groups are incorporated in said stem and at least one branch.

2. The method of claim 1, wherein said stem and said at least one branch further comprise a plurality of sugar moieties and the nucleobases are attached to said sugar moieties to form nucleosides.

3. The method of claim 2, wherein the label-attracting groups are separately attached to some of said nucleosides such that the distance between the middles of two consecutive nucleosides with said label-attracting groups attached is less than the length of an oligonucleotide consisting of 18 nucleotides.

4. The method of claim 3, wherein said distance between the middles of two consecutive nucleosides with said label-attracting groups attached is more than the length of an oligonucleotide consisting of 3 nucleotides.

5. The method of claim 3, wherein the label-attracting groups and the backbone are linked by a spacer so that the distance between each label-attracting group and said backbone is individually a distance of at least 4 atoms.

6. The method of claim 1, wherein the stem has a sugar-phosphate backbone comprising alternating moieties of sugar and phosphate.

7. The method of claim 1, wherein the stem has a polyamide backbone comprising amido bonds.

8. The method of claim 1, wherein the label-attracting group comprises a hapten.

9. The method of claim 8, wherein the hapten is digoxigenin, nitrophenol, lactosamine, a 4-hydroxy-3-nitro-phenacetyl group, (N-hydroxysuccinimidyl)-ε-aminocaproyl-(4-hydroxy-3-nitro-phenacetyl)-carboxamide, 4-hydroxy-3-iodo-5-nitro-phenacetyl group, (N-hydroxysuccinimidyl)-ε-aminocaproyl-(4-hydroxy-3-iodo-5-nitro-phenacetyl)-carboxamide or 1-dimethoxy trityl-3-O-(N-(2,4-dinitrophenyl)-3-aminopropyl)-triethylene glycol)-glyceryl-2-O-(cyanoethyl)-(N,N-diisopropyl)-phosphoramide.

10. The method of claim 9, wherein the hapten is digoxigenin.

11. A kit for the determination of a substance, comprising a probe and a conjugate, wherein the probe is a branched molecule comprising
   a plurality of nucleobases,
   at least two non-nucleosidic label-attracting groups, wherein said label-attracting groups are groups detectable directly or indirectly,
   a stem, and
   at least one branch, wherein the label-attracting groups are in said stem and at least one branch,
wherein the conjugate has a molecular weight of no more than 100 kDa and comprises a signal-producing component and a group that has an affinity for the label-attracting group.

12. A method of detecting a substance in a sample, comprising
   1) contacting the sample with a probe under conditions in which said substance if present binds directly or indirectly to the probe to produce a binding product, which probe comprises a plurality of nucleosides and at least two non-nucleosidic label-attracting groups, wherein said label-attracting groups are separately attached to some of said nucleosides such that the distance between the middle of two consecutive nucleosides with said label-attracting groups attached is less than the length of an oligonucleotide consisting of 18 nucleotides, but more than the length of an oligonucleotide consisting of 3 nucleotides;
   2)
      a) mixing the binding product with a conjugate, which conjugate comprises a signal-producing component and a group that has an affinity for the label-attracting group to produce a mixture containing a conjugate-bound product, wherein said conjugate has a molecular weight of no more than 100 kDa,
      b) removing unbound conjugate from said mixture,
      c) determining the presence of the conjugate-bound product in said mixture by means of said signal-producing component, and thereafter
      d) using the presence of the conjugate-bound product as an indicator of the presence of the binding product; and
   3) using the presence of the binding product as an indicator of the presence of said substance.

13. The method of claim 12, wherein the probe is a branched molecule comprising at least one branch covalently attached to at least one branching point of said molecule.

14. The method of claim 12, wherein the signal-producing component is aequorin.

15. The method of claim 12, wherein the label-attracting group comprises a hapten.

16. The method of claim 15, wherein the hapten is digoxigenin, nitrophenol, lactosamine, a 4-hydroxy-3-nitro-phenacetyl group, (N-hydroxysuccinimidyl)-ε-aminocaproyl-(4-hydroxy-3-nitro-phenacetyl)-carboxamide, 4-hydroxy-3-iodo-5-nitro-phenacetyl group, (N-hydroxysuccinimidyl)-ε-aminocaproyl-(4-hydroxy-3-iodo-5-nitro-phenacetyl)-carboxamide or 1-dimethoxy trityl-3-O-(N-(2,4-dinitrophenyl)-3-aminopropyl)-triethylene glycol)-glyceryl-2-O-(cyanoethyl)-(N,N-diisopropyl)-phosphoramide.

17. The method of claim 16, wherein the hapten is digoxigenin.

18. A probe for detecting a substance, comprising
   (I) an analyte-binding region, which directly or indirectly binds said substance; and
   (II) an amplification region, which comprises a plurality of nucleobases and at least two non-nucleosidic label-attracting groups, wherein said label-attracting groups are separately attached to some nucleosides such that the distance between the middle of two consecutive nucleosides with said label-attracting groups attached is less than the length of an oligonucleotide consisting of 18 nucleotides, but more than the length of an oligonucleotide consisting of 3 nucleotides, wherein said label-attracting groups are detected using a conjugate, which conjugate comprises a signal-producing component and a group that has an affinity for the label-attracting group, and wherein said conjugate has a molecular weight of no more than 100 kDa.

19. The probe of claim 18, wherein the probe is a branched molecule comprising at least one branch covalently attached to at least one branching point on said molecule.

20. The probe of claim 18, wherein the label-attracting group comprises a hapten.

21. The probe of claim 20, wherein the hapten is digoxigenin, nitrophenol, lactosamine, a 4-hydroxy-3-nitro-phenacetyl group, (N-hydroxysuccinimidyl)-ε-aminocaproyl-(4-hydroxy-3-nitro-phenacetyl)-carboxamide, 4-hydroxy-3-iodo-5-nitro-phenacetyl group, (N-hydroxysuccinimidyl)-ε-aminocaproyl-(4-hydroxy-3-iodo-5-nitro-phenacetyl)-carboxamide or 1-dimethoxy trityl-3-O-(N-(2,4-dinitrophenyl)-3-aminopropyl)-triethylene glycol)-glyceryl-2-O-(cyanoethyl)-(N,N-diisopropyl)-phosphoramide.

22. The probe of claim 21, wherein the hapten is digoxigenin.

* * * * *

SEQUENCE LISTING

<160> NUMBER OF SEQ ID NOS: 7

<210> SEQ ID NO 1
<211> LENGTH: 27
<212> TYPE: DNA
<213> ORGANISM: Artificial Sequence
<220> FEATURE:
<221> NAME/KEY: misc_binding
<222> LOCATION: (1)..(27)
<223> OTHER INFORMATION: The nucleotide in position 1 contains biotin
      bound. The symbol n means 3-amino-1,2-propane-diol, elongated
      with 6-amino-hexanoic acid and labeled with
      digoxigenin-N-hydroxysuccinimide-ester.
<220> FEATURE:
<223> OTHER INFORMATION: Description of Artificial Sequence:
      Oligodesoxyribonucleotide

<400> SEQUENCE: 1 ttttttata ngggcatntg gtggnct                                              27

<210> SEQ ID NO 2
<211> LENGTH: 31
<212> TYPE: DNA
<213> ORGANISM: Artificial Sequence
<220> FEATURE:
<221> NAME/KEY: misc_feature
<222> LOCATION: (1)
<223> OTHER INFORMATION: n means DNP bound with DNP-TEG.
<220> FEATURE:
<223> OTHER INFORMATION: Description of Artificial Sequence:
      Oligodesoxyribonucleotide

<400> SEQUENCE: 2 ntttttttt tatagggca tttggtggtc t                                          31

<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: (1)
<223> OTHER INFORMATION: at the 5' end biotin is bound via aminolinker
      AMII (Boehringer Mannheim).
<220> FEATURE:
<223> OTHER INFORMATION: Description of Artificial Sequence:
      Oligodesoxyribonucleotide -continued

```
<400> SEQUENCE: 3
agaccaccaa atgcccctat                                                    20

<210> SEQ ID NO 4
<211> LENGTH: 41
<212> TYPE: DNA
<213> ORGANISM: Artificial Sequence
<220> FEATURE:
<221> NAME/KEY: misc_feature
<222> LOCATION: (1)
<223> OTHER INFORMATION: at the 5'-end DNP is bound via DNP-TEG.
<220> FEATURE:
<221> NAME/KEY: misc_feature
<222> LOCATION: (11)
<223> OTHER INFORMATION: n means DNP bound via DNP-TEG.
<220> FEATURE:
<223> OTHER INFORMATION: Description of Artificial Sequence:
      Oligodesoxyribonucleotide

<400> SEQUENCE: 4
nttttttttt nttttttttt tatagggca tttggtggtc t                             41

<210> SEQ ID NO 5
<211> LENGTH: 51
<212> TYPE: DNA
<213> ORGANISM: Artificial Sequence
<220> FEATURE:
<221> NAME/KEY: misc_feature
<222> LOCATION: (1)
<223> OTHER INFORMATION: n means DNP bound via DNP-TEG.
<220> FEATURE:
<221> NAME/KEY: misc_feature
<222> LOCATION: (21)
<223> OTHER INFORMATION: n means DNP bound via DNP-TEG.
<220> FEATURE:
<223> OTHER INFORMATION: Description of Artificial Sequence:
      Oligodesoxyribonucleotide

<400> SEQUENCE: 5
nttttttttt tttttttttt nttttttttt tatacgggca tttggtggtc t                 51

<210> SEQ ID NO 6
<211> LENGTH: 65
<212> TYPE: DNA
<213> ORGANISM: Artificial Sequence
<220> FEATURE:
<221> NAME/KEY: misc_feature
<222> LOCATION: (1)
<223> OTHER INFORMATION: n means DNP bound via DNP-TEG.
<220> FEATURE:
<221> NAME/KEY: misc_feature
<222> LOCATION: (11)
<223> OTHER INFORMATION: n means DNP bound via DNP-TEG.
<220> FEATURE:
<221> NAME/KEY: misc_feature
<222> LOCATION: (24)
<223> OTHER INFORMATION: n means DNP bound via DNP-TEG.
<220> FEATURE:
<221> NAME/KEY: misc_feature
<222> LOCATION: (29)
<223> OTHER INFORMATION: n means AM III maleinimido or AM
      III-maleinimido-S-tttttttttnttttttttttnt-3',
      wherein n means DNP incorporated via DNP-TEG.
<220> FEATURE:
<221> NAME/KEY: misc_feature
<222> LOCATION: (34)
<223> OTHER INFORMATION: n means DNP bound via DNP-TEG.
<220> FEATURE:
<221> NAME/KEY: misc_feature
<222> LOCATION: (39)
<223> OTHER INFORMATION: n meanshere AM III maleinimido or AM
      III-maleinimido-S-tttttttttnttttttttttnt-3',
      wherein n means DNP incorporated via DNP-TEG.
```

-continued

```
<220> FEATURE:
<223> OTHER INFORMATION: Description of Artificial Sequence:
      Oligodesoxyribonucleotide

<400> SEQUENCE: 6
nttttttttt ntttttttt tttntttnt tttntttnt ttttataggg gcatttggtg      60
gttct                                                               65

<210> SEQ ID NO 7
<211> LENGTH: 61
<212> TYPE: DNA
<213> ORGANISM: Artificial Sequence
<220> FEATURE:
<221> NAME/KEY: misc_feature
<222> LOCATION: (1)
<223> OTHER INFORMATION: n means DNP bound via DNP-TEG.
<220> FEATURE:
<221> NAME/KEY: misc_feature
<222> LOCATION: (11)
<223> OTHER INFORMATION: n means DNP bound via DNP-TEG.
<220> FEATURE:
<221> NAME/KEY: misc_feature
<222> LOCATION: (21)
<223> OTHER INFORMATION: n means DNP bound via DNP-TEG.
<220> FEATURE:
<221> NAME/KEY: misc_feature
<222> LOCATION: (26)
<223> OTHER INFORMATION: n means AM III-maleinimido or AM
      III-maleinimido-S-tttttttttnttttttttttnt-3',
      wherein n means DNP bound via DNP-TEG.
<220> FEATURE:
<221> NAME/KEY: misc_feature
<222> LOCATION: (31)
<223> OTHER INFORMATION: n means DNP bound via DNP-TEG.
<220> FEATURE:
<221> NAME/KEY: misc_feature
<222> LOCATION: (36)
<223> OTHER INFORMATION: n means AM III-maleinimido or AM
      III-maleinimido-S-tttttttttnttttttttttnt-3',
      wherein n means DNP bound via DNP-TEG.
<220> FEATURE:
<223> OTHER INFORMATION: Description of Artificial Sequence:
      Oligodesoxyribonucleotide

<400> SEQUENCE: 7
nttttttttt ntttttttt nttttntttt nttttntttt tatagggca tttggtggtc    60 t                                                                   61
```